United States Patent [19]

Lash

[11] Patent Number: 4,710,189

[45] Date of Patent: Dec. 1, 1987

[54] SHAPED DISPOSABLE DIAPERS WITH SHAPED ELASTICALLY CONTRACTIBLE WAISTBANDS

[75] Inventor: Glen R. Lash, Cincinnati, Ohio

[73] Assignee: The Procter & Gamble Company, Cincinnati, Ohio

[21] Appl. No.: 21,074

[22] Filed: Mar. 3, 1987

Related U.S. Application Data

[63] Continuation of Ser. No. 756,416, Jul. 18, 1985, abandoned, which is a continuation of Ser. No. 476,734, Mar. 18, 1983, abandoned.

[51] Int. Cl.[4] .............................................. A61F 13/16
[52] U.S. Cl. ................................................ 604/385 A
[58] Field of Search ................... 604/385.1, 385.2, 358

[56] References Cited

U.S. PATENT DOCUMENTS

| 4,337,771 | 7/1982 | Pieniak et al. | 604/385.2 |
| 4,388,075 | 6/1983 | Mesek et al. | 604/385.2 |
| 4,437,860 | 3/1984 | Sigl | 604/385.2 |
| 4,527,990 | 7/1985 | Sigl | 604/385.2 |

Primary Examiner—John D. Yasko
Attorney, Agent, or Firm—John M. Pollaro; Fredrick H. Braun; Richard C. Witte

[57] ABSTRACT

Disposable diapers having elasticized waistbands which are shaped to conform to the wearers' waists and methods of making them. The shaped disposable diapers are made by affixing an elastomeric material having a heat unstable state and a heat stable and elastic state to the diaper while the elastomeric material is in its heat unstable state and then heating the elastomeric material while the diaper is restrained in a folded configuration.

5 Claims, 11 Drawing Figures

SHAPED DISPOSABLE DIAPERS WITH SHAPED ELASTICALLY CONTRACTIBLE WAISTBANDS

This is a continuation of application Ser. No. 756,416, filed on July 18, 1985, now abandoned, which in turn is a continuation of application Ser. No. 476,734 filed on Mar. 18, 1983, now abandoned.

BACKGROUND OF THE INVENTION

Field of the Invention

This invention concerns shaped disposable diapers, incontinent briefs, and the like having elastically contractible waistbands.

Background Art

Infants (and other incontinents) wear disposable diapers to receive and contain urine, feces, and other body fluids. Disposable diapers function both to contain the discharged materials and to isolate these materials from the body of the wearer and from the wearer's surroundings. Modern embodiments of disposable diapers frequently perform these tasks in a manner superior to that of traditional cloth diapers.

Disposable diapers normally comprise three elements: a liquid permeable topsheet designed to be placed next to the wearer's skin; a liquid impermeable backsheet which forms, in use, the outer surface of the diaper; and an absorbent element interposed between the topsheet and the backsheet.

The topsheet is frequently a hydrophobic non-woven fabric which is readily permeable to fluid. It hydrophobicity tends to cause the surface in contact with the wearer's skin to be dry and the skin to be protected from fluids absorbed within the absorbent element.

The absorbent element receives and retains fluids which pass through the topsheet. It normally comprises a batt of airlaid wood pulp fibers.

The backsheet functions to contain fluids within the absorbent element thereby protecting the wearer's outer garments and other surfaces from soiling by these fluids. Backsheets are commonly formed of fluid impermeable, vapor impermeable materials such as polyethylene film.

Disposable diapers having many different basic designs are known to the art. For example, Duncan and Baker in U.S. Pat. No. Re 26,152, issued Jan. 31, 1967, describe and claim a disposable diaper which has achieved wide acceptance and commercial success. Buell, in U.S. Pat. No. 3,860,003, issued Jan. 14, 1975, describes and claims another disposable diaper which, too, has achieved wide acceptance and commercial success. The diaper taught by Buell differs from that taught by Duncan and Baker in many respects, not the least of which is the provision in the Buell diaper of elasticized (or contractible) leg cuffs. Another embodiment of disposable diapers is described and claimed by Aziz and Blaney in European Patent Application No. 82200801.7, filed June 29, 1982. The Aziz and Blaney diaper also provides elasticized (or contractible) leg cuffs, but is of a somewhat different design than that described by Buell.

Mesek et al in U.S. Pat. No. 4,324,245 issued Apr. 13, 1982; Pieniak et al in U.S. Pat. No, 4,337,771, issued July 6, 1982; and Mesek et al in U.S. Pat. No. 4,352,355, issued Oct. 5, 1982 describe disposable diapers having elasticized cuffs and elasticized (or contractible) waistbands.

Strickland and Visscher in U.S. Pat. No. 4,253,461, issued on Mar. 3, 1981, describe and claim another form of disposable diaper sometimes referred to as an incontinent brief and intended to be worn by adults.

While the disposable diapers described above, particularly those described by Duncan and Baker, Buell, and Aziz and Blaney, functin in exemplary manner, disposable diapers comprising fluid and vapor impermeable backsheets have sometimes been perceived as being somewhat hot and uncomfortable. Further, diapers provided with such impermeable backsheets are unable to self-dry as they otherwise would because evaporation of fluids from the absorbent element is precluded. To counteract this perception, and to permit self-drying, backsheets which are relatively impermeable to liquid but relatively permeable to vapor and which are known as breathable backsheets have been described. Breathable backsheets tend to provide a cooler garment and permit some measure of self-drying of the diaper while it is being worn. For example, Crowe, Jr. in U.S. Pat. No. 3,156,242, issued on Nov. 10, 1964, teaches the use of a microporous film as a breathable backsheet. Hartwell, in U.S. Pat. No. 3,881,489, issued on May 6, 1975, teaches a breathable backsheet comprising, in combination, two layers: a low-void volume perforated thermoplastic film and a porous high-void volume hydrophobic tissue. Sisson, in U.S. Pat. No. 3,989,867, issued on Nov. 2, 1976, teaches a breathable backsheet provided with tapered hollowed bosses which prevent the passage of liquid while allowing vapor to pass readily therethrough. Obenour, in U.S. Pat. No. 4,341,216, issued July 27, 1982, describes and claims a still different embodiment of a breathable backsheet.

The above cited ten patents and patent application are incorporated herein by reference.

Another improved diaper comprises an elastically contractible waistband which allows the diaper to breathe and which tends to resist waistband rollover. These benefits are achieved by providing disposable diapers with a waistband comprising an elastic element interposed between the topsheet and the backsheet and affixed to both the topsheet and the backsheet in such a way as to cause the formation of transverse channels between the topsheet and the elastic element and the backsheet and the elastic element Transverse in this context means extending across ("transverse to") the waistband and that the channels extend from the otuer diaper margin to an interior region of the diaper.

While the diapers described above are useful, developments providing more comfortable and serviceable diapers have still been sought.

SUMMARY OF THE INVENTION

The present invention is of a shaped disposable diaper comprising a shaped elastically contractible waistband and of a method for making such a shaped disposable diaper. More particularly, the shaped disposable diaper of the present invention is, at least in part, held in its shaped configuration by the shaped elastically contractible waistband. The elastically contractible waistband is itself specially formed and comprises an elastomeric material which has both a heat unstable state and a heat stable and elastic state (hereinafter referred to, for convenience, simply as "elastomeric material"). "Elastic" is used here to describe a material which can be elongated to a practical extent upon the application of tension and which will substantially return to its original configuration after the tension is released. In the context of the present invention, the heat stable state is dimensionally smaller than the heat unstable state. The elastomeric material is applied to the disposable diaper in its heat unstable state. The disposable diaper is folded into a preselected orientation, is restrained in that orientation, and is heated to such an extent as to cause the elastomeric material to assume its heat stable and elastic state. The resulting elastically contractible waistband assumes an essentially permanent set related to the folded configuration, which essentially permanent set tends to cause the disposable diaper to be shaped and to fit more closely about the trunk of the wearer. The resulting waistband also tends to resist waistband rollover.

DETAILED DESCRIPTION OF THE INVENTION

Figure 1:
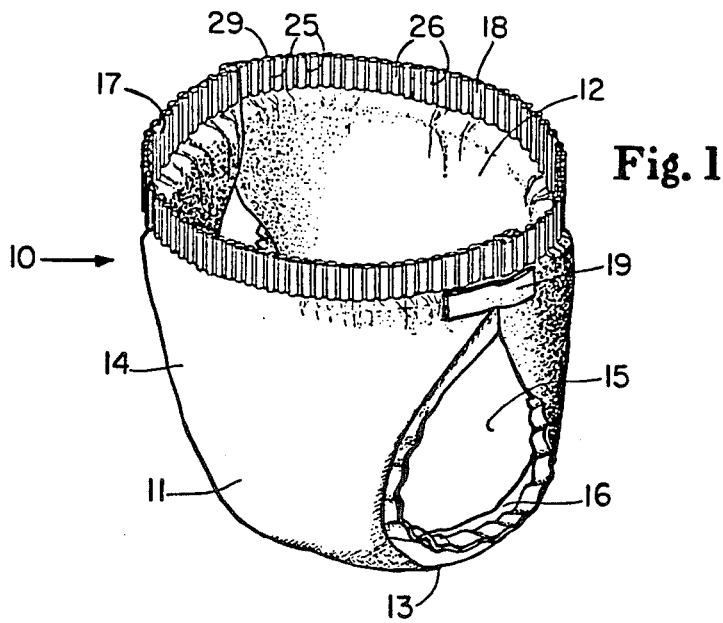
FIG. 1 is a perspective view of a prior art disposable diaper embodying an elastically contractible waistband and in a configuration as applied to an infant.

While this specification concludes with claims particularly pointing out and distinctly claiming the subject matter regarded as the invention, it is believed that a better understanding of the invention can be achieved through careful reading of the following detailed description of the invention in conjunction with study of the attached drawings and the appended example.

Disposable diapers comprise three major elements: a topsheet; a backsheet; and an absorbent element. The topsheet forms the inside of the disposable diaper (i.e., that portion intended to be placed next to the wearer's skin). The backsheet generally forms the exterior surface of the disposable diaper. The absorbent element is interposed between the topsheet and the backsheet.

A disposable diaper is generally designed to be placed between and generally centered between the legs of an infant and secured about the infant by bringing the front portion of the diaper adjacent the front waist area of the infant and the rear portion of the diaper adjacent the rear waist area of the infant and securing the diaper in that position.

Optionally, disposable diapers comprise fastening tapes for securing the diaper about the infant. They also optionally comprise elastic members in the longitudinally extending margins to form an elastically contractible leg cuff or side flap. They also optionally comprise elastic elements in the laterally extending margins to form elastically contractible waistbands.

The waistband of a disposable diaper is that portion of the diaper which is intended to be placed adjacent the wearer's waist. While the waistband can comprise a separate element affixed to the bosy of the disposable diaper, it more often is an extension of other elements of the disposable diaper such as the backsheet or the topsheet or both the backsheet and the topsheet. Further, the waistband is generally considered to be that portion of the diaper extending from the laterally extending margin of the diaper to about the laterally extending margin of the absorbent element. Disposable diapers are normally constructed so as to have two waistbands: a front and a rear. While disposable diapers can be constructed so as to have a single unitary waistband encircling the waist of the wearer, such designs are not preferred. It is also possible to construct a disposable diaper having three or more waistband sections intended to be affixed about the waist of the wearer, but, these embodiments, too, are not preferred.

The present invention provides a shaped disposable diaper having at least one elastically contractible waistband. Further, the elastically contractible waistband comprises an elastomeric material having both a heat unstable state and a heat stable and elastic state. The elastomeric material is attached to the disposable diaper when the elastomeric material is in its heat unstable state; the elastomeric material is then heated under certain, defined conditions in such a manner that it assumes its heat stable but elastic state.

Massengale et al in U.S. Pat. No. 3,819,401, issued June 25, 1974 and Koch et al in U.S. Pat. No. 3,912,565, issued Oct. 14, 1975, both incorporated herein by reference, teach a technique for preparing shirred, or gathered, elastic garments. In this technique, a heat contractible material is affixed to the garment when the heat contractible material is in its elongated and heat unstable state. The entire system is then heated thereby causing the heat contractible material to contract to its heat stable but elastic state thereby shirring, or gathering the garment.

Any prior art disposable diaper, such as those taught by Duncan and Baker or by Buell and by Aziz and Blaney, comprising an absorbent core interposed between a topsheet and a backsheet, can incorporate the teachings of Massengale et al and Koch et al by having a strip of an elastomeric material (hereinafter defined in greater specificity) applied laterally across the width of the disposable diaper in one or both of its waist regions. Typically, the absorbent core does not extend fully to the lateral (waist) edges of the topsheet and backsheet which are typically coextensive. The elastomeric material is conveniently interposed between the top sheet and the backsheet in that region between the termination of the absorbent core and the termination of the esssentially coextensive topsheet and backsheet. A simple disposable diaper is shown in partially cut away plan view in FIG. 10.

Figure 10:
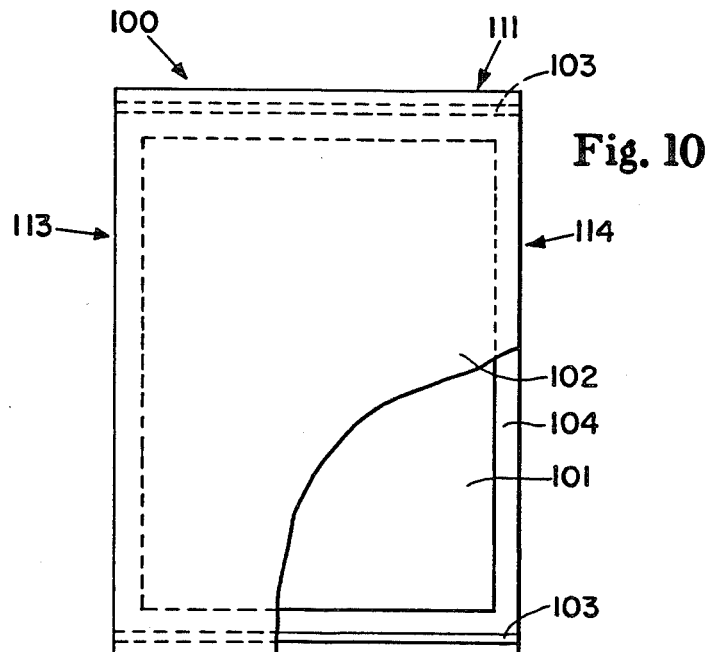
FIG. 10 is a partialy fragmented plan view of a simple disposable diaper.

In FIG. 10, simple disposable diaper 100 comprises absorbent core 101 interposed between topsheet 102 and backsheet 104. Diaper 100 has longitudinal side margins 113 and 114. It also has lateral waist regions 111 (rear) and 112 (front). Strips of elastomeric material 103 are interposed between topsheet 102 and backsheet 104 and extend laterally across the diaper in that region between the termination of absorbent core 101 and the lateral edges of diaper 100. Elastomeric material strips 103 are affixed to both topsheet 102 and backsheet 104 by means not illustrated.

It must be noted that reference numerals are used consistently throughout all the figures and that the thicknesses of certain materials in the figures have been exaggerated for clarity.

Figure 6:
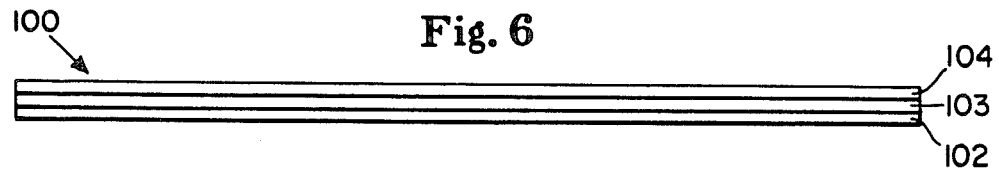
FIG. 6 is a simplified schematic representation of an end view of the disposable diaper of FIG. 10, which diaper has an elastomeric material in the waistband; the elastomeric material is shown in its heat unstable state.

FIG. 6 is an end view of diaper 100 as looking toward rear waist are 111. In this view, the thicknesses of the three elements have been exaggerated for clarity.

Figure 7:
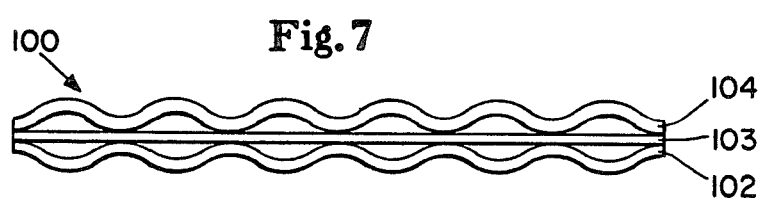
FIG. 7 is a simplfied schematic end view of the disposable diaper shown in FIG. 6 after the elastomeric material has assumed its heat stable and elastic state.

FIG. 7 is the same view of diaper 100 as shown in FIG. 6, but represents diaper 100 after elastomeric material strip 103 has been subjected to sufficient thermal energy to cause it to contract prdominantly uniaxially. It can be readily seen that the contraction of elastomeric material strip 103 gathers, or shirrs, topsheet 102 and backsheet 104 more or less uniformly over their entire common lengths. This is what one obtains if one merely applies the teachings of Massengale et al or Koch et al to disposable diapers.

It has been surprisingly discovered that if the garment to which the elastomeric material is attached is a disposable diaper comprising an absorbent core, and if the diaper is folded while the elastomeric material is in its heat unstable form, the elastomeric material will contract nonuniformly when heated. Nonuniform contraction results in (1) nonuniform gathering of the materials attached to the elastomeric material; (2) a tendency of the diaper to retain a configuration analogous to its folded configuration; and (3) a decreased tendency to waistband rollover when the diaper is worn. The benefits flowing from a shaped configuration are better fit and decreased leakage around the waistband.

Figure 8:
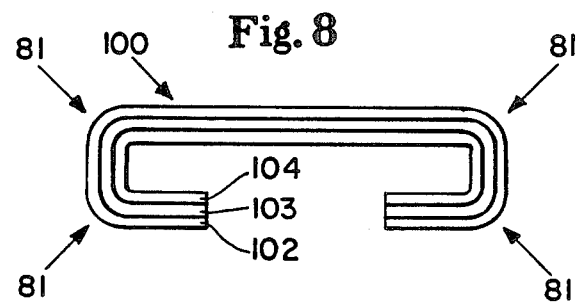
FIG. 8 is a simplfied schematic representation of the end of the disposable diaper of FIG. 10, which diaper has elastomeric material in the waistband, which diaper has been folded into a C-fold configuration; the elastomeric material is shown in its heat unstable state.

FIG. 8 is the same end view of diaper 100 as shown in FIG. 6 except that diaper 100 has been folded into a C-fold configuration and is held in that configuration by means not shown. Diaper 100 has four fold areas 81 illustrated. The C-fold shown in this figure is an open C-fold. Closed folds where topsheet 102 actually contacts itself on the inner surfaces of the "C" are not only possible, but also are preferred in many situations.

Figure 9:
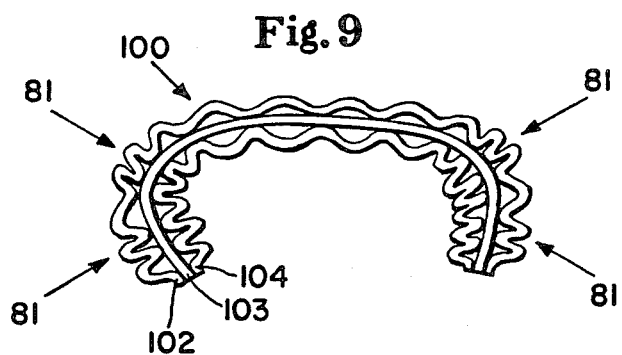
FIG. 9 is a simplified schematic representation of the disposable diaper shown in FIG. 8 after the elastomeric material has assumed its heat stable and elastic state.

FIG. 9 is a view of diaper 100 analogous to that shown in FIG. 8, except this view is taken after elastomeric material strip 103 has been subjected to sufficient thermal energy to cause it to substantially contact to its heat stable and elastic state. In FIG. 9, the restraining means associated with, but not shown in, FIG. 8, has been removed. It is to be notd that disposable diaper 100 retains a general "C" configuration, although not nearly so sharply defined as the C-fold configuration shown in FIG. 8. Further, it is to be noted that neither topsheet 102 nor backsheet 104 is uniformly gathered as shown in FIG. 7. They are, in fact, more gathered, or shirred, in fold regions 81 than in regions outside fold regions 81.

While expressing an intention not to be bound by the following comments, it can be theorized that the benefits of the present invention flow from a tendency of the absorbent core to resist the contraction of the elastomeric material in those regions where the absorbent core is intact. The bending of the absorbent core, as at the folds, tends to decrease the amount of resistance the core engenders thereby allowing the elastomeric material to contract more fully in the regions associated with the folds.

The elasomeric materials useful in the present invention include a number of materials well known to those skilled in the art. For example, the polyurethane described in the hereinbefore incorporated patent to Koch et al and the plasticized vinyl chloride described in the hereinbefore incorporated patent to Massengale et al can be used. Further, the compositions comprising a mixture of a thermoplastic resin material (or other organic, normally sold heat flowable material) in an elastomeric material as described by Cook in U.S. Pat. No. Re 28,688, incorporated herein by reference, can also be used.

A preferred elastomeric material useful herein is a blend of ethylene propylene rubber with ethylene vinyl acetate which has been extruded into a film as made by Exxon Chemical Company of Florham Park, N.J., and which has been tentered. During tentering, the film is placed in an oven at approximately 65° C. and, after softening, it is stretched to approximately four times its original length in one direction. The stretched film is then allowed to cool. The polymers are now predominantly uniaxially oriented and the film essentially retains its new dimension and is in a heat unstable state. (It should be noted that this particular material is still elastic even in its heat unstable state.) Subsequent treatment of the film as with heated air at about 68° C. is sufficient to cause to film to reassume its heat stable and elastic state.

A diaper embodiment in which the present invention finds preferred utility is illustrated in FIG. 1 through 5.

FIG. 1 is a perspective view of a prior art disposable diaper, but one in which the present invention is preferred for use. The diaper illustrated in FIG. 1 is based on the disposable diaper design taught in the hereinbefore incorporated patent to Buell. (While this is a preferred diaper design for use in the present invention, it must be realized that the present invention can be used, and is contemplated for use, with other disposable diaper designs. Several such designs are described in the hereinbefore incorporated patents and European patent application; other designs can be readily envisioned by those skilled in the art.)

Referring now to FIG. 1, disposable diaper 10 is shown in perspective in a configuration as if it were applied about an infant. Disposable diaper 10 comprises a front portion 11 and a rear portion 12 with a crotch portion 13 interposed therebetween. In use, crotch portion 13 is placed between the legs of the infant and front portion 11 and rear portion 12 are placed, respectively, along the front and rear lower portions of the wearer's trunk. Topsheet 15 forms the inner surface of disposable diaper 10 while backsheet 14 forms its outer surface. Side flaps (or leg cuffs) 16 fit about the wearer's thighs. In use, front waistband 17 and rear waistband 18 are placed adjacent the wearer's waist regions on, respectivley, the front and rear portions of the wearer's trunk. Disposable diaper 10 is held in position about the wearer by fastening tape 19. Outer margin of waistband 29 is shown in FIG. 1 as the upper edge of disposable diaper 10. Transverse regions of securement 25 and transverse regions of non securement 26 in the waistbands are discussed more fully hereinafter.

Figure 2:
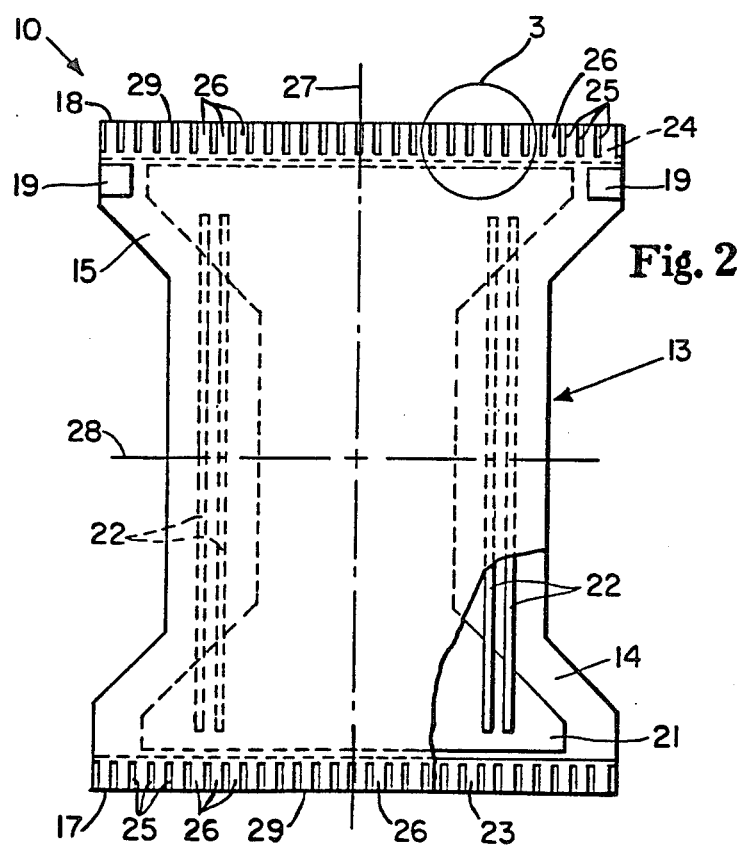
FIG. 2 is a partially fragmented plan view of the disposable diapers shown in FIG. 1 and in FIG. 11, but in an unfolded configuration.

FIG. 2 is a partially cut away plan view of disposable diaper 10 opened out into a planar configuration. Topsheet 15 is, in this illustration, the upper surface of the diaper while backsheet 14 is the lower surface. Absorbent element 21 is interposed between topsheet 15 and backsheet 14.

As illustrated, disposable diaper 10 is generally symmetrical about longitudinal center line 27 and lateral center line 28. While this is a preferred configuration, it is not necessary that disposable diaper 10 by symmetrical. An asymmetric orientation about lateral center line 28, as when crotch portion 13 is transposed toward front waistband 17, is quite useful.

Disposable diaper 10 is provided with elastic members 22 in the side margins thereof running generally parallel to longitudinal center line 27. In the embodiment illustrated, two elastic members 22 are placed on either side of disposable diaper 10; single or multiple elastic members can be used. The embodiment illustrated is, however, preferrred.

Fastening tapes 19 are secured to disposable diaper 10 adjacent rear waistband 18.

Front waist elastomeric element 23 and rear waist elastomeric element 24 are positioned, respectively, in front waistband 17 and rear waistband 18 adjacent outer margin of waistband 29. In the embodiment illustrated in FIGS. 1 and 2, disposable diaper 10 comprises elastic waist elements in both the front and the rear waistbands. While this is a preferred embodiment, the present invention is useful in diaper designs having only the front or only the rear waistband elasticized.

Transverse regions of securement 25 and transverse regions of nonsecurement 26 are also illustrated in FIG. 2.

One major function of backsheet 14 is to prevent body fluids from escaping from disposable diaper 10 and soiling the wearer's outer garments and other surfaces in contact with the disposable diaper. Any compliant, non-irritating planar material which is impermeable to body fluids can be used as backsheet 14. Suitable materials are described with particularity in the hereinbefore incorporated patents and patent application. A preferred backsheet is formed from polyethylene film having a thickness of from about 0.012 to about 0.051 millimeter (mm).

Breathable backsheets (i.e. backsheets that permit the passage of vapor and air while retarding the passage of liquid) useful in the present invention are described in the hereinbefore incorporated patents to Crow, Jr., Hartwell, Sisson, and Obenour.

The size of backsheet 14 is dictated by the exact diaper design selected and the size of the infant intended to be the wearer; it can be readily ascertained by those skilled in the art.

Topsheet 15 can be any compliant, soft feeling, non-irritating (to the wearer's skin) planar material. It functions to contact the wearer's skin, to receive fluid discharges, to allow the discharges to pass readily therethrough into the absorbent element, and to isolate the wearer's skin from the fluids in the absorbent element. To aid in effective performance of the last function, the topsheet is preferably hydrophobic.

Topsheet 15 can be porous paper made from natural or synthetic fibers or mixtures thereof, non-woven fabric made from natural or synthetic fibers or mixtures thereof, apertured plastic film, porous foam, or the like. Examples of suitable topsheets are described in the hereinbefore incorporated patents and patent application.

A preferred topsheet is spun bonded non-woven polyester fabric made from fibers of from about 2.2 to about 2.5 denier, having a basis weight of about 17 grams (g) per square meter ($M^2$). Another preferred topsheet material has a basis weight of 22 g per $M^2$ and comprises about 65% (by weight) staple length, 1.5 denier polyester fibers (such as Kodel type 411 polyester fibers as sold by Tennessee Eastman Corporation, Kingsport, Tenn.); about 15% crimped, staple length, 1.5 denier rayon fibers; and about 20% acrylic copolymer binder (such as Celanese CPE 8335 as sold by Celanese Corporation of Charlotte, N.C.). "Staple length" refers to fibers having a length of at least about 15 mm.

Still another preferred topsheet is constructed from polypropylene fibers which have been carded and thermally bonded in a spaced-apart pattern. Fibers about 3.8 centimeters (cm) long and of from about 1.5 to about 3.0 denier are suitable. A preferred topsheet of this type has a basis weight of about 24 g per $M^2$.

Suitable topsheets can also be constructed from apertured plastic films such as those described by Radel and Thompson in U.S. Pat. No. 4,342,314, issued Aug. 3, 1982; Ferguson and Landrigan in U.S. Pat. No. 4,341,217, issued July 27, 1982; and Thompson in U.S. Pat. No. 3,929,135, issued Dec. 30, 1985. These three patents are incorporated herein by reference.

As with the case of backsheet 14, the size of topsheet 15 is dictated by the exact diaper design selected.

Absorbent element 21 can be any means which is generally compressible, conformable, non-irritating to the wearer's skin, and which is capable of absorbing and retaining fluids.

Absorbent element 21 can be constructed from any of a variety of materials commonly used in disposable absorbent articles and which are described in the hereinbefore incorporated patents. Examples of suitable absorbent materials include creped cellulose wadding, absorbent foams, absorbent sponges, super absorbent polymers, and, preferably, comminuted and airlaid wood pulp fibers commonly referred to as absorbent fluff. An absorbent fluff having a density of from about 0.05 to about 0.175 g per $cm^3$ is generally acceptable.

As in the case of backsheet 14 and topsheet 15, the size of absorbent element 21 is dictated by the exact diaper design selected.

Optionally, absorbent element 21 can have associated with either or both planar faces envelope tissues (not illustrated in the drawings) comprising any permeable material well known to those skilled in the art, such as wet strength tissue paper. When used, envelope tissues are generally coextensive with absorbent element 21 and either coterminus therewith or folded up and about the laterally extending margins thereof. Envelope tissues can optionally be secured to absorbent core 21 by any means well known to those skilled in the art.

Absorbent element 21 is interposed between backsheet 14 and topsheet 15. The diaper design selected determines whether or not the three elements are coterminus although, in general, either backsheet 14 or topsheet 15 or both extend beyond the margins of absorbent element 21. In the present invention, both backsheet 14 and topsheet 15 preferrably extend beyond the laterally extending margins of absorbent element 21 and are essentially coterminus along their laterally extending margins.

Optionally, backsheet 14 can be secured to absorbent element 21 by any convenient means (not illustrated in the drawings) well known to those skilled in the art.

Examples of suitable means are parallel beads of adhesive (such as hot melt adhesive) and double sided adhesive tape; each extend essentially the entire longitudinal length of absorbent element 21.

Elastic members 22 serve to contract or gather the cuffs (longitudinally extending margins) of disposable diaper 10 and maintain them in contact with the legs of the wearer thereby providing improved fit and reducing fluid leakage from the diaper. One material which can be used for elastic elements 22 is an elastic tape having a cross section of about 0.18 mm by from about 1.5 mm to about 6.4 mm and made from natural rubber as available from East Hampton Rubber Company of Stuart, Va., under the trademark L-1900 Rubber Compound. Other suitable elastic members can be made from natural rubber elastic tapes sold under the trademarks Fulflex 9211 and Fulflex 9111 by Fulflex Company, of Scotland, N.C.

The length of elastic elements 22 is dictated by the precise diaper design chosen. In the design illustrated in FIGS. 1 and 2, elastic elements 22 extend a major portion of the longitudinal length of disposable diaper 10, but terminate outside the waist regions of disposable diaper 10.

Elastic members 22 are operably associated with disposable diaper 10 by securing them to the diaper adjacent its longitudinally extending margins by elastic attachment means which are not shown in the Figures. The elastic attachment means should be flexible and of sufficient adhesiveness to hold elastic members 22 in their stretched condition substantially indefinitely. One suitable means is hot melt adhesive. A more detailed description of the manner in which elastic members 22 should be positioned and secured to disposable diaper 10 is given in the hereinbefore incorporated patent to Buell.

Elastic members 22 are affixed to disposable diaper 10 in an elastically contractible condition so that in a normally unrestrained configuration elastic members 22 effectively contract or gather the diaper material adjacent elastic members 22. Elastic members 22 can be affixed to disposable diaper 10 in an elastically contractible condition in at least two ways. For example, elastic members 22 can be stretched to an elongated orientation and affixed to disposable diaper 10 while disposable diaper 10 is in an uncontracted condition. Alternatively, disposable diaper 10 can be contracted (in crotch portion 13, for example by pleating) and elastic members 22 can be affixed to the contracted disposable diaper 10 while the elastic members are in their relaxed or unstretched orientation.

Front waist elastomeric element 23 and rear waist elastomeric element are each formed of elastomeric material as hereinbefore described. Waist elastomeric elements 23 and 24 are at least about 0.6 cm wide, preferably at least about 1.6 cm wide. While the maximum width of waist elastomeric elements 23 and 24 is determined by the diaper design and matters of economy, they generally are no wider than about 3.8 cm.

In the embodiment illustrated in FIGS. 1 and 2 waist elastomeric elements 23 and 24 each extend across essentially the entire lateral width of disposable diaper 10. While this is a preferred construction, the present invention is useful in designs wherein waist elements 23 and 24 extend across only a portion of the lateral width of the diaper. Waist elastomeric elements 23 and 24 should, however, extend across a major portion of the lateral width of disposable diaper 10.

The topsheet, backsheet, and each waist elastomeric element are affixed together by transverse regions of securement while the waist elastomeric elements are in their heat unstable state and all three elements are essentially fully, but not elastically, extended. The system is later heated (as with heated air) and the waist elastomeric element is allowed to return to its heat stable and elastic state.

Figure 3:
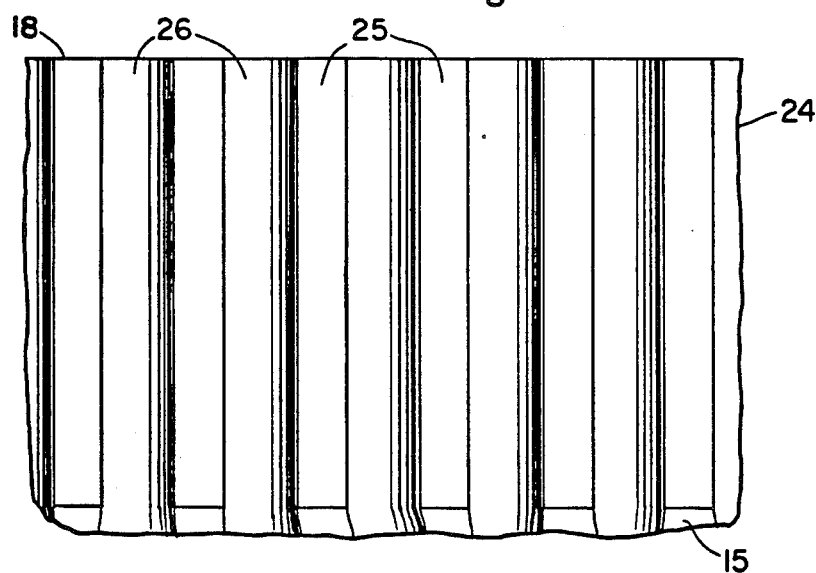
FIG. 3 is an enlarged partial view of the waistband of the diaper of FIG. 1 illustrating one preferred embodiment of an elastically contractible waistband.
Figure 4:
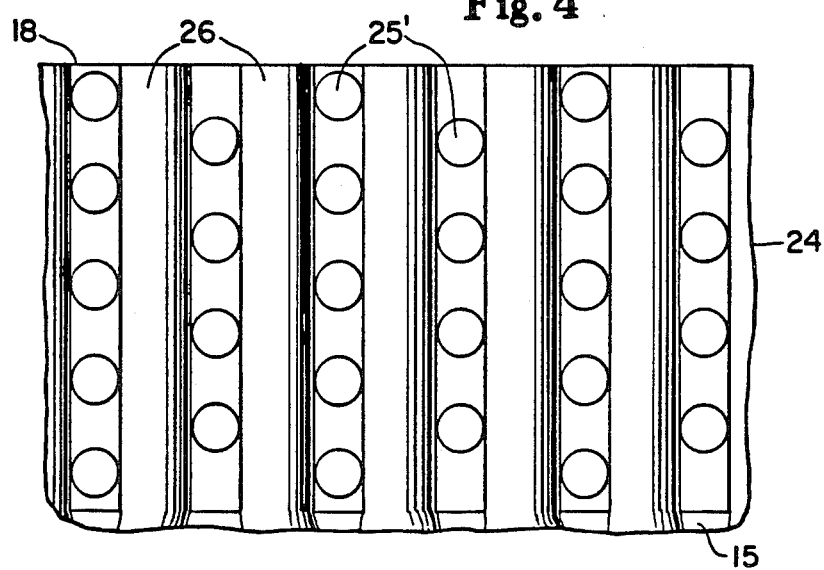
FIG. 4 is an enlarged partial view of the waistband of the diaper of FIG. 1 illustrating another preferred embodiment of an elastically contractible waistband.

Transverse regions of securement 25 are shown in a generalized representation in FIGS. 1 and 2. More specific embodiments of transvese regions of securement 24 are depicted in FIGS. 3 and 4 which are enlarged views of a portion of rear waistband 18 indicated by reference numeral 3 in FIG. 2. In these views, the elastomeric material is in its heat stable and elastic state.

In this discussion of FIGS. 3 and 4, reference shall be made to rear waistband 18 and the components thereof. The same comments can be made about front waistband 17 and its components.

Transverse regions of securement 25 extend essentially across the whole width of waist elastomeric element 24.

The term "transverse" as used in this context refers to an orientation generally perpendicular to the major laterally extending dimension of waistband 18. That is to say, since rear waistband 18 extends laterally across the width of disposable diaper 10 and is generally parallel to lateral center line 28, the transverse regions of securement 25 extend across rear waistband 18 in an orientation essentially parallel to longitudinal center line 27; they are directed generally from outer margin of waistband 29 to the center of disposable diaper 10. As illustrated, transverse regions of securement 25 are shown to be at essentially right angles to lateral center line 28 and to the lateral extent of waistband 18. This is the preferred orientation. One can, however, depart from true transversity without destroying the benefits conferred. The departure from true (or absolute) transversity becomes to great when channels (as hereinafter discussed) are no longer formed extending essentially across the width of waistband 18. In general, departure from transversity becomes too great for practical operation of the present invention when the departure from transversity exceeds about 45° from true transversity (or perpendicularity to lateral center line 28).

The term "essentially across" is used in this context to indicate that transverse regions of securement 25 need not extend absolutely across the entire width of waist elastomeric element 24 so long as they extend sufficiently far across the width thereof to provide the channels discussed hereinafter.

In FIG. 3, transverse regions of securement 24 are shown as essentially regularly spaced unitary zones of sealing attaching waist elastomer element 24 to topsheet 15 and backsheet 14 which is not visible in FIG. 3 or 4. The precise means for providing the zones of sealing can be readily selected by those skilled in the art. Examples include adhesive attachment, solvent sealing and the like. Preferably, ultrasonic welding is used.

Figure 5:
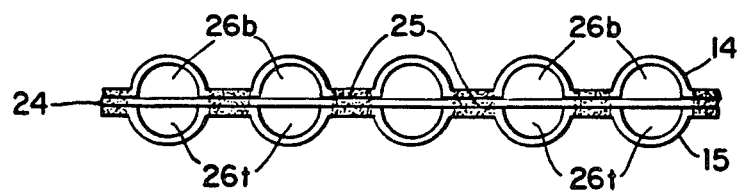
FIG. 5 is an end view of the portion of the waistbands shown in FIGS. 3 and 4.

As illustrated in FIGS. 3, 4, and 5, the points of attachment of both topsheet 15 and backsheet 14 to waist elastomeric element 24 are in register (i.e. are coextensive). This is a preferred orientation, but the points of attachment of topsheet 15 to waist elastomeric element 24 can be offset from the adjacent points of attachment of backsheet 14 to waist elastomeric element 24. In such a situation there will be offset transverse regions of securement on either side of the waist elastomeric element.

FIG. 4 illustrates an alternate embodiment of transverse regions of securement 25'. In this embodiment, the transverse regions of securement comprise discrete spaced zones of sealing, preferably ultrasonic welds, effectively attaching the materials together and forming the channels hereinafter described. Preferably the discrete spaced zones are circular or elliptical.

Transverse regions of securement 25 can be from about 0.15 to about 1.0 cm wide (i.e. in the dimension generally parallel to lateral centerline 28. They are preferably regularly spaced, but they can be nonuniformly spaced. They are preferably from about 0.3 to about 1.5 cm apart are measured from center to center.

FIG. 5 illustrates the functioning of the transverse regions of securement. FIG. 5 is an end view of the portions of rear waistband 18 shown in FIG. 3 and FIG. 4 with rear waist elastomeric element 24 in its heat stable and elastic state. In FIG. 5, transverse regions of securement 25 are shown as darkened portions for emphasis. Topsheet 15 and backsheet 14 are shown gathered. These gathers constitute and define transverse regions of nonsecurement 26b between backsheet 14 and rear waist elastomeric element 24 and transverse regions of nonsecurement 26t between topsheet 15 and rear waist elastomeric element 24. These transverse regions of nonsecurement 26b and 26t form open gathers or channels from the margin of the diaper extending to the interior of the diaper and terminating in the region adjacent the laterally extending edges of absorbent element 21. These open channels allow the diaper to breathe by allowing the exchange of air and vapor between the interior of the diaper and the surrounding atmosphere even when the diaper is secured about an infant.

At the same time as transverse regions of nonsecurement 26b and 26t are formed, topsheet 15 and backsheet 14 form structures in the nature of corrugations. These corrugations extend transversely across the width of rear waistband 18 tend to stiffen the waistband thereby tending to prevent waistband rollover (i.e., the bending of the waistband about itself).

Figure 11:
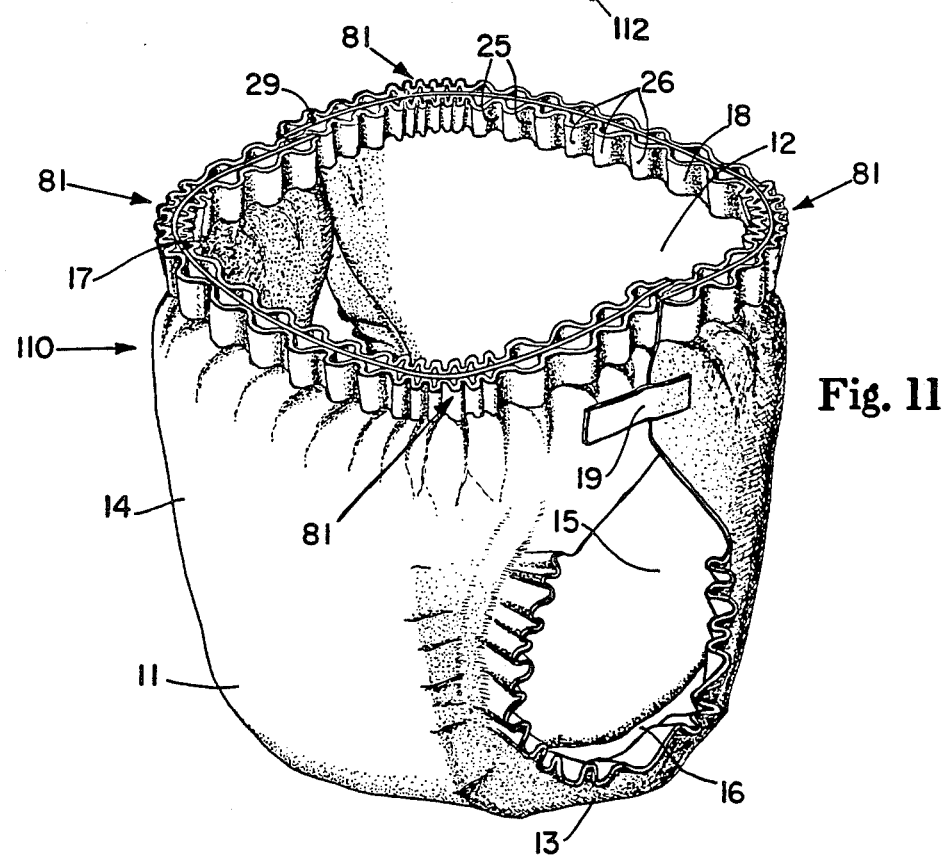
FIG. 11 is a perspective view of a diaper of the invention and is a configuration as applied to an infant.

As noted hereinbefore, the diaper illustrated in FIG. 1 does not embody the teachings of the present invention. That is to say, when the diaper was heated to cause the waist elastomeric elements to change from their heat unstable state to their heat stable and elastic state, the diaper was in an unrestrained, generally planer configuration. As illustrated in FIG. 1, relatively unifrom corrugations and channels were produced. A diaper 110 made as the diaper of FIG. 1, but treated according to the teachings of this invention, is shown in FIG. 11. Before heating the diaper to cause the waist elastomeric elements to change from their heat unstable state to their heat stable and elastic state, the front and rear waist regions 17 and 18 were folded into a closed C-fold configuration as indicated in FIG. 8. The diaper was restrained in this configuration during the heating. Following the heating operation, which converted the waist elastomeric elements to their heat stable and elastic state, and after the restraining means were removed, front waistband 17, rear waistband 18, and diaper 110 exhibited generally shaped configurations even in the absence of securement with adhesive tapes 19. The size of the corrugations in channels was not uniform with the corrugations and channels being smaller in regions of fold 81. Thus, FIG. 11 illustrates a diaper of the present invention.

As indicated hereinbefore, the diaper embodiments described in some detail are preferred embodiments. Other diaper designs embodying elastically contractible waistbands can benefit from the teachings of this invention.

In the foregoing discussion, the elastomeric material which was affixed to the diaper in an unstable state and was then treated to cause it to be transformed into a stable and elastic state has been discussed in terms of a "heat unstable" elastomer. More broadly, the elastomeric materials useful herein are those materials that have an unstable state relative to some other stable and elastic state and which can be caused to be transformed from the unstable to the stable state by the application of any form of energy or by any other convenient treatment. The most convenient and the most practical form of energy is heat and the materials are described in such terms herein. The form of energy can be any other similar form of energy such as ultraviolet, infrared, microwave, or gamma radiation.

Still further, the present invention has been described in terms of an elastomeric material which is affixed to the diaper in its unstable state and is later transformed to its stable and elastic state. While, in general, the stable state is an absolute state, it is not necessary that it be. It is only required that the state following treatment be relatively more stable than the state preceeding treatment and that the state following treatment be sufficiently stable for practical use. It is, of course, necessary that the material be elastic in its stable state.

EXAMPLE

Diapers according to the present invention are constructed following the basic design described in the aforementioned patent to Buell. This diaper design provides for two (front and rear) waistbands.

The absorbent element comprises absorbent fluff having a density of about 0.09 g per $cm^3$ and a basis weight of about 1100 g per $M^2$ in the crotch portion and about 350 g per $M^2$ near the waist portions. It is generally hourglass-shaped and is about 38.7 cm long, about 25.4 cm wide at each of its laterally extending margins, and about 9.6 cm wide in the crotch portion. It is symmetrical about its longitudinal center line, but asymmetrical about its lateral center line in that the crotch portion is centered about 21.6 cm from the rear lateral margin.

The topsheet comprises the thermally bonded polypropylene material hereinbefore mentioned and the backsheet 0.04 mm thick polyethylene film. Both also are hourglass-shaped and are about 43.8 cm long and about 30.5 cm wide at their laterally extending margins.

During construction, the absorbent element is interposed between the topsheet and the backsheet which are essentially coextensive and coterminus. Hot-melt adhesive glue beads running parallel to the longitudinal center line secure the backsheet to the absorbent element. They also secure the backsheet to the topsheet in the cuff regions.

The cuff portions of the diapers are elasticized by incorporating therein two elastic members in each longitudinally extending margin of the diaper at the crotch portion. Each is made of Fulflex 9211 and is 2.4 mm wide and 0.18 mm thick; their relaxed length is about 19.6 cm. They are extended to about 220% of their original lengths at the time of attachment. These elastic members are centered about the crotch portion. The pattern defined by the pair of members is centered about 9.4 cm from the longitudinal center line of the diaper and parallel thereto. The two elastic members in each diaper margin are centered on parallel lines about 1.6 cm apart.

Each diaper waistband extends the lateral width of the diaper and is about 30.5 cm long; each waistband is about 2.5 cm wide in the transverse direction. The waist elastomeric element used in each waistband is the hereinbefore described ethylene propylene rubber blended with ethylene vinyl acetate which is tentered as described. Each is about 30.5 cm long, and 2.5 cm wide, and about 0.04 mm thick and is secured to both the topsheet and the backsheet. At the time of securement the topsheet and the backsheet are in fully extended configurations.

Transverse regions of securement comprising discrete zones of ultrasonic welds are used to affix each waist elastomeric element to both the topsheet and to the backsheet. The transverse regions of securement each comprise seven discrete elliptical zones of ultrasonic welds each having a major axis of about 1.9 mm and a minor axis of about 1.0 mm; each individual ellipse is set with its major axis at an angle of about 45° to the transverse direction. The transverse regions of securement are generally regularly spaced along each waistband and their centers are about 6.4 mm apart.

Adhesive fastening tapes were adhesively affixed to the diaper.

Each assembled diaper is folded in a closed C-fold as described above and several are restrained in that configuration. The folded diaper is heated with air at about 68° C. so that the elastomeric material shrinks to its heat stable and elastic state. The diapers of this invention exhibit different degrees of gathering along the waist band when the restraining force is removed and the diapers are allowed to assume a loose "C" configuration.

When worn by infants, these diapers perform in a satisfactory manner and the waistbands thereof tend to conform more effectively about infants' waists than do similar diapers which are subjected to heat treatment while unrestrained.

What is claimed is:

1. A disposable diaper comprising:
   a liquid permeable topsheet;
   a liquid impermeable backsheet, said backsheet being affixed to said topsheet;
   an absorbent element, said absorbent element being interposed between said backsheet and said topsheet;
   a waistband extending from the laterally extending margin of the diaper to about the laterally extending margin of said absorbent element;
   fold regions at which said topsheet and said backsheet are folded; and
   an elastomeric element, said elastomeric element being affixed to said waistband, said elastomeric element having a middle portion of relatively less contraction and a pair of additional portions of relatively more contraction compared to said middle portion, said additional portions being separated by said middle portion.

2. The disposable diaper of claim 1 wherein said elastomeric element gathers said waistband nonuniformly.

3. The disposable diaper of claim 2 wherein said elastomeric element tends to gather said waistband into a C-shaped configuration.

4. The disposable diaper of claim 1 wherein said elastomeric element has a nonelastic heat unstable state and an elastic heat stable state.

5. A diaper as recited in claim 1 wherein said elastomeric element comprises:
   a further two portions, separated by said middle portion and said pair of additional portions, and of relatively less contraction compared to said additional portions.

* * * * *

UNITED STATES PATENT AND TRADEMARK OFFICE
CERTIFICATE OF CORRECTION

PATENT NO. : 4,710,189

DATED : December 1, 1987

INVENTOR(S) : Glen R. Lash

It is certified that error appears in the above-identified patent and that said Letters Patent is hereby corrected as shown below:

```
Column 1, at line 32:  delete "it" and insert --its--
Column 3, at line 47:  delete "the" and insert --this--
Column 4, at line 15:  delete "bosy" and insert --body--
Column 4, at line 53:  delete "and by" and insert --or by--
Column 5, at line 17:  delete "are" and insert --area--
Column 5, at line 53:  delete "contact" and insert --contract--
Column 5, at line 56:  delete "notd" and insert --noted--
Column 6, at line 5:   delete "elasomeric" and insert --elastomeric--
Column 6, at line 13:  delete "sold" and insert --solid--
Column 6, at line 60:  delete "tivley" and insert --tively--
Column 10, at line 11: delete "24" and insert --25--
Column 10, at line 40: delete "to" and insert --too--
Column 10, at line 53: delete "24" and insert --25--
Column 11, at line 12: delete "28." and insert --28).--
Column 11, at line 15: delete "are" and insert --as--
```

Signed and Sealed this

Third Day of May, 1988

Attest:

DONALD J. QUIGG

Attesting Officer

Commissioner of Patents and Trademarks